United States Patent [19]

Anderson et al.

[11] Patent Number: 4,798,791

[45] Date of Patent: Jan. 17, 1989

[54] VECTOR FOR HIGH LEVEL GENE EXPRESSION

[75] Inventors: David M. Anderson, Rockville; Jeffrey C. McGuire, Frederick, both of Md.

[73] Assignee: Genex Corporation, Gaithersburg, Md.

[21] Appl. No.: 671,967

[22] Filed: Nov. 16, 1984

[51] Int. Cl.$^4$ .................. C12P 21/00; C12P 19/34; C12N 5/00; C12N 7/00

[52] U.S. Cl. ...................... 435/68; 435/70; 435/91; 435/172.3; 435/317; 435/320; 935/6; 935/22; 935/29; 935/48; 935/73; 536/27

[58] Field of Search .............. 435/68, 71, 91, 253, 435/317, 172.3; 536/27; 935/6, 29, 22, 41, 48, 56, 72, 40, 60, 73

[56] References Cited

U.S. PATENT DOCUMENTS 4,643,969  2/1987  Inouye et al. .................. 435/68
4,666,848  5/1987  Gelfand et al. .

OTHER PUBLICATIONS

Wu et al., (1981) *Proceedings National Academy Sciences*, USA, vol. 78, pp. 2913–2917.
Holmes et al. (1983), *Cell*, vol. 32, pp. 1029–1032.
Platt et al. (1985, Mtg. Held) *UCLA Symp. on Molecular and Cellular Biol.*, New Ser., vol. 30, pp. 151–160.
Schmeissner, U., et al., *J. Mol. Biol.* 176: 39–53 (1984).
Platt, T., et al., in, R. Calendar and L. Gold, eds., *Sequence Specificity in Transcription and Translation*, Alan R. Liss, Inc., Publisher, New York, New York (1985).
Holmes et al., *Cell*, 32:1029–1032 (1983).
Guarente et al., *J. Mol. Biol.*, 133:189–197 (1979).
Chernajovsky et al., *Annals of the New York Academy of Science*, 413:88–96 (1983).
Platt, T., *The Operon*, pp. 290–294, Cold Spring Harbor, New York (1978).
Mellor et al., *Gene*, 24:1–14 (1983).
Wu et al., *Cell*, 19:829–836 (1980).
Mott, J. E., *The American Biology Teacher*, 46:388–393 (1984).

*Primary Examiner*—Thomas G. Wiseman
*Assistant Examiner*—S. Seidman
*Attorney, Agent, or Firm*—Saidman, Sterne, Kessler & Goldstein

[57] ABSTRACT

Methods and vectors for high level expression of genes in bacteria are disclosed. A terminal mRNA sequence from a gene coding for a stable bacterial protein mRNA is ligated to a gene coding for the desired protein adjacent the translation termination codon of the gene. The gene for the desired protein and the terminal mRNA sequence are situated in an expression vector in which the gene is operably linked to a transcription promoter.

23 Claims, 2 Drawing Sheets

VECTOR FOR HIGH LEVEL GENE EXPRESSION

BACKGROUND OF THE INVENTION

The use of recombinant DNA technology has made possible the large scale production in fermentation facilities of proteins which would otherwise have to be isolated from natural sources. In the application of this technology, a microorganism such as a bacterium is transformed with a replicable expression vector containing a gene which codes for a protein not normally produced by the bacterial host, i.e., a heterologous protein. The gene for the heterologous protein is operably linked to a regulatory sequence of DNA, including a transcription promoter, which is capable of directing expression of the gene in the bacterial host. Due to the universality of the genetic code, the bacterial host is capable of transcribing the heterologous gene into messenger RNA (mRNA) and then translating the mRNA into protein having the amino acid sequence of the heterologous protein.

Over the last several years, a great deal of research in the recombinant DNA field has focused on methods for improving the efficiency with which transformed microorganisms can be made to express heterologous genes in order to improve yields of desired products. Efforts at improving levels of heterologous gene expression have been primarily directed at manipulation of "upstream" DNA components—that is, DNA sequences which precede the heterologous gene in the expression vector and affect the frequency and efficiency of transcription—and at controlling post-translational events which affect product stability or recovery. The latter approach is exemplified by efforts to develop host-vector combinations which effect secretion of the translated heterologous protein through the cell wall of the host cell and into the surrounding medium where it is less subject to degradative attack by proteases produced in the host cell.

While considerable improvements have been made in obtainable levels of gene expression and product recovery, the art continues to seek methods by which heterologous genes can be expressed and the expression products recovered in increased amounts.

SUMMARY OF THE INVENTION

This invention provides methods for expressing genes coding for desired proteins in bacteria at elevated levels of expression. In accordance with the method of the invention, the 3' terminal sequence found in the mRNA from a gene coding for a protein native to the bacterial host is ligated, in the form of its complementary DNA, to a structural gene for the desired protein adjacent the translation termination signal of the gene. The gene for the desired protein having the terminal mRNA nucleotide sequence ligated thereto is situated in a vector that is replicable in the bacterial host such that the gene is operably linked to a transcription promoter. The bacterium is then transformed with this vector. The transformant is grown up and the gene expressed using conventional techniques. A preferred terminal mRNA nucleotide sequence for use in the method of the invention is the trpt sequence of the E. coli tryptophan operon.

There is also provided a replicable expression vector for expressing a desired protein in a bacterium. The replicable expression vector comprises a structural gene for any desired protein operably linked to a transcription promoter; and a terminal mRNA nucleotide sequence from a gene coding for a protein native to a bacterium, said terminal sequence being adjacent the translation termination codon of the desired gene.

DETAILED DESCRIPTION AND PREFERRED EMBODIMENTS

Figure 1:
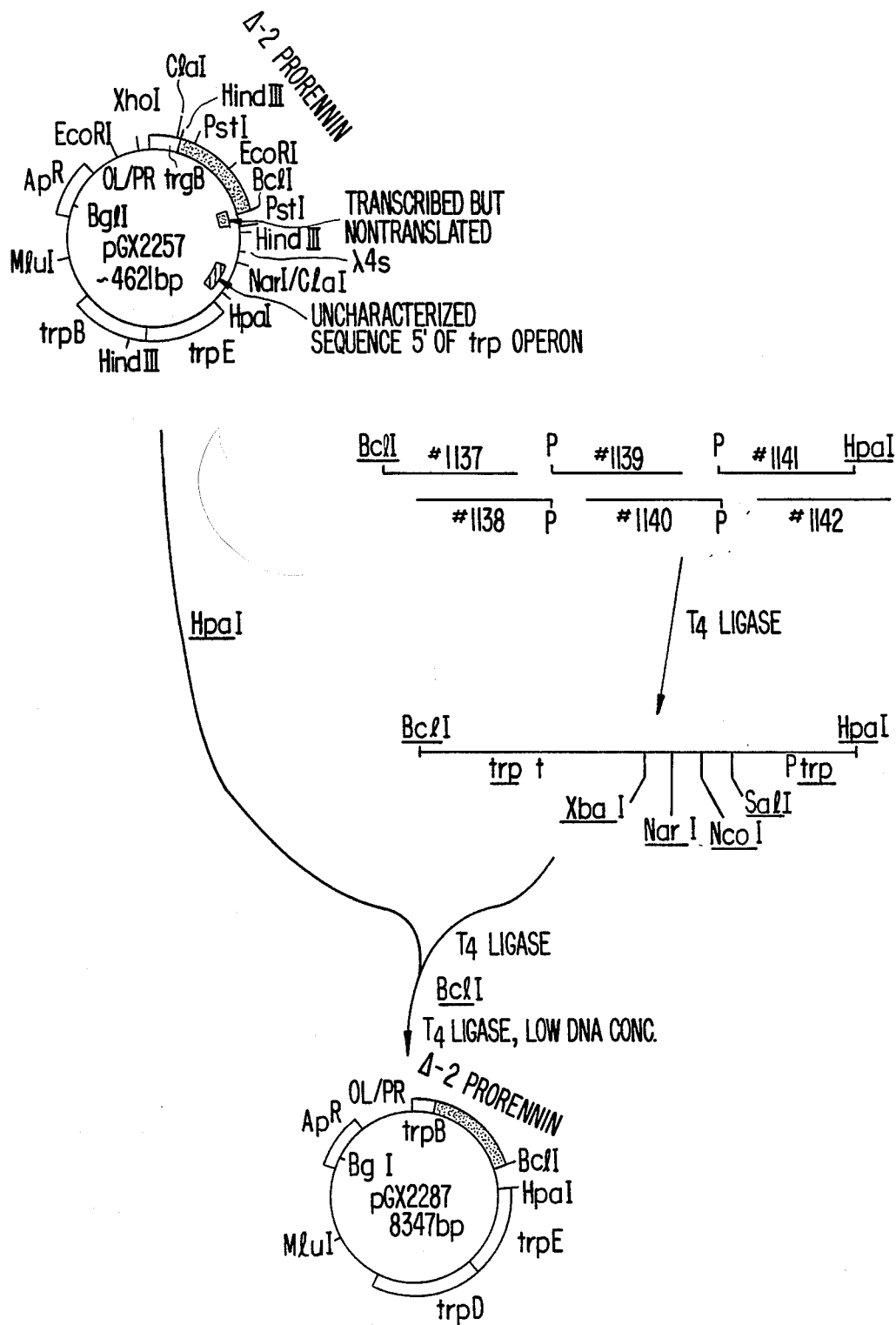
FIG. 1 is a schematic representation of the construction of plasmid pGX2287, which contains the trpt sequence just 3' to the translation termination sequence of a gene coding for Δ-2 prochymosin.

While not wishing to be bound by any particular theory of the mechanism by which increased expression levels are effected in accordance with the invention, it is believed that the insertion of a terminal mRNA sequence from a bacterial gene at the 3' end of the desired gene, i.e., just downstream from the translation termination signal, results in production of mRNA of increased stability.

In vitro evidence suggests that the E. coli trpt sequence may not be a strong terminator of transcription (Holmes, et al., Cell, 32:1029–1032 [1983]) and that transcription termination of the trp operon in E. coli may occur in vivo downstream from the trpt sequence (Guarente, et al., J. Mol. Biol., 133:189–197 [1979]). One interpretation of these data is that transcription termination takes place 3' of trpt followed by rapid degradation of mRNA up to the trpt sequence. That is, the trypt sequence may act as a degradation stop signal, thereby stabilizing the mRNA. By placing a terminal mRNA sequence such as trpt at the end of a heterologous gene, degradation of mRNA into the structural gene is inhibited. Advantageously, insertion of the trpt sequence is accompanied by removal of normally transcribed but untranslated DNA at the 3' end of the heterologous gene. Removal of untranslated sequence at the 3' end of the gene may reduce the probability of nuclease sensitive sites being present in the mRNA and avoids expending energy on the synthesis of unnecessary mRNA.

In accordance with the practice of the invention, a terminal mRNA sequence of a gene coding for a stable bacterial protein mRNA is ligated to the 3' end of the gene for the desired protein. As used herein, the phrase "terminal mRNA sequence" refers to the untranslated portion of a gene for a bacterial protein that codes for the 3' end of a stable mRNA for the bacterial protein. The terminal mRNA sequence may or may not be the point at which transcription actually terminates during formation of the bacterial protein mRNA. If it is not, however, it corresponds to the 3' terminus of the stable form of the mRNA.

Preferably, the terminal mRNA sequence is derived from a gene for a protein which is produced in relative abundance by the bacterial host. Suitable terminal mRNA sequences for use in the invention include the trypt sequence of the E. coli tryptophan operon, and terminal RNA sequences from mRNA that codes for abundant E. coli proteins such as the omp, rpo, rps, rpm, rpl genes or other genes terminal in operons that code for abundant proteins or proteins that become abundant after induction. Unlike trypt, in some cases the actual terminal stable mRNA sequence has not yet been determined. Thus, one could either determine the terminal sequence of isolated mRNA using known techniques or utilize the entire sequence between the termination codon and apparent transcription termination sites predicted from DNA sequence. It is preferable, however, to utilize a characterized sequence that has been determined at the end of a stable mRNA since it may not always be possible to accurately predict transcription termination sites from DNA sequence (especially rho dependent termination sites). Preferably, the terminal mRNA sequence employed is the trpt sequence of the *E. coli* tryptophan operon. This is a 34-nucleotide DNA sequence which follows the stop codon (TAA) at the end of the trpA gene.

Figure 2:
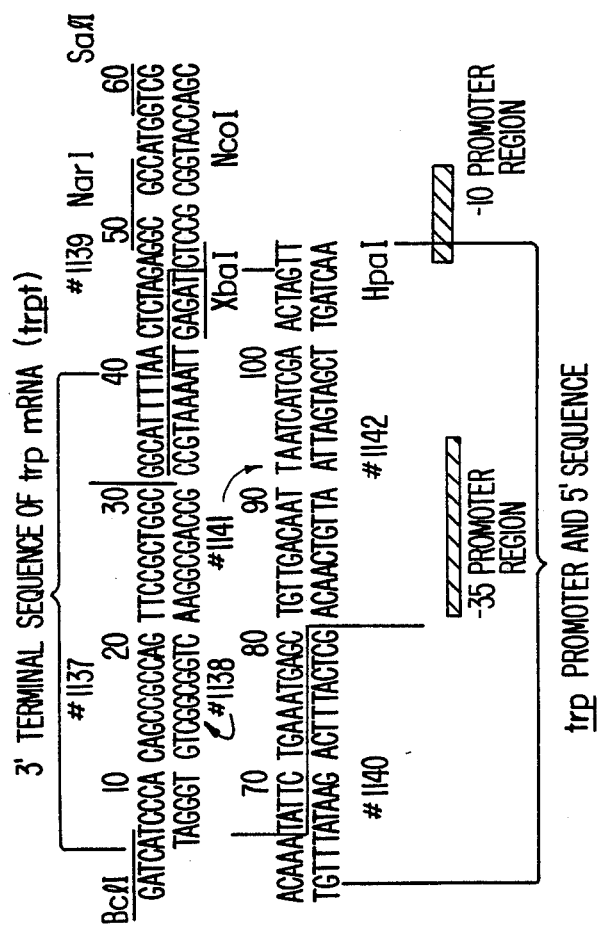
FIG. 2 illustrates the DNA sequence of assembled synthetic oligodeoxynucleotides, including the trypt sequence, which were inserted adjacent the translation termination codon of the Δ-2 prochymosin gene.

Referring to FIG. 2, the trpt sequence is that portion of the synthetic oligodeoxynucleotide beginning at nucleotide no. 5, ATCC..., and ending at nucleotide no. 39, ... TTTT. The terminal mRNA sequence which is inserted at the 3' end of the heterologous gene is preferably obtained by techniques of oligonucleotide synthesis. We produced the oligonucleotides shown in FIG. 2 using standard phosphoramidite methods (S. L. Beaucage and M. H. Caruthers, *Tetrahedron Lett.*, 22:1859 [1981]); M. D. Matteucci and M./ H. Caruthers, *Tetrahedron Lett.*, 21:719 [1980]); M. D. Matteucci and M. H. Caruthers, *J. Am. Chem. Soc.*, 103:3185 [1981]) and a commercially available oligonucleotide synthesis machine from Applied Biosystems, Inc.

While the invention is exemplified below with respect to expression of prochymosin, it will be readily understood that the methods of the invention are equally applicable to the expression of genes coding for virtually any heterologous protein or even a non-heterologous protein (different from the protein corresponding to the terminal mRNA sequence), where expression amplification of the non-heterologous gene is desired. Many such genes have already been cloned and inserted into expression vectors in which they are operably linked to transcription promoters and other regulatory sequences which direct and control gene expression in bacterial hosts. Any known expression vectors, including plasmids and phages, which are capable of replication in bacterial hosts, can be employed in the practice of the invention. Likewise, any known promoters which are capable of directing transcription of heterologous genes in bacterial hosts can be employed. These include, for example, the trp promoter, trp/lac hybrid promoter, λ $O_L/P_R$ promoter (derived from the leftward operator and rightward promoter of phage λ) and other known promoters.

The expression vector of the invention can be produced by modification of an existing expression vector containing a gene for the desired protein operably linked to a transcription promoter. Referring to FIG. 1, we produced an expression vector of the invention for high level expression of prochymosin (pGX2287) starting with plasmid pGX2257. Plasmid pGX2257 contains a structural gene for Δ-2 prochymosin (prochymosin less its first two amino acids), fused at its 5' end to a trpB gene, under the control of the λ $O_L/P_R$ hybrid promoter. The Δ-2 prochymosin gene in pGX2257 contains a 228-base pair transcribed but untranslated region following the translation termination codon. The untranslated region was removed by endonuclease cleavage, first with HpaI and then with BclI. A synthetic oligonucleotide (FIG. 2) containing the trpt sequence on a BclI-HpaI fragment, was inserted immediately downstream from the translation termination codon. The insert was constructed to contain a number of convenient restriction sites 3' to the trpt sequence so that the Δ-2 prochymosin gene and trpt sequence could easily be transferred to other vectors.

It is preferred to insert the terminal transcription sequence of the bacterial protein as close as possible to the 3' end of the translation termination codon of the gene for the desired protein. It may be difficult or impossible to have it contiguous with the translation termination signal without the use of synthetic DNA, site directed mutagenesis, or exonuclease treatment depending on the location of convenient endonuclease sites. The requirement that the terminal mRNA sequence be "adjacent the translation termination signal" of the gene for the desired protein is satisfied if there are no more than about 100 nucleotides, preferably no more than about 3 nucleotides, separating the last nucleotide of the translation termination codon of the gene for the desired protein and the first nucleotide of the terminal mRNA sequence from the stable bacterial protein mRNA.

The expression vector of the invention containing the gene coding for the desired protein operably linked to a transcription promoter and the terminal mRNA sequence adjacent to the translation termination signal is used to transform a bacterial host such as an *E. coli* in a conventional manner. The transformed bacteria are then grown up in a fermentor and subjected to conditions under which the gene for the desired protein is expressed. We have found that *E. coli* strain GX1731 transformed with plasmid pGX2287 produced considerably higher titers of prochymosin than the same host strain transformed with the parental plasmid, pGX2257, under similar fermentation conditions.

The following examples are intended to further illustrate the practice of the invention and are not intended to limit the scope of the invention in any way.

EXAMPLE 1

Construction of Plasmid pGX2287

Referring to FIG. 2, each of the single-strand oligonucleotides identified as #1137, 1138, 1139, 1140, 1141 and 1142 were synthesized using standard phosphoramidite methods (S. L. Beaucage and M. H. Caruthers, *Tetrahedron Lett.*, 22:1859 (1981); M. D. Matteucci and M. H. Caruthers, *Tetrahedron Lett.*, 21:719 (1980); M.D. Matteucci and M. H. Caruthers, *J. Am. Chem. Soc.*, 103:3185 (1981)) and a commercially available oligonucleotide synthesis machine (Applied Biosystems). The oligonucleotides were purified using HPLC and adjusted to a concentration of 1.0 $A_{260}$ unit per ml of $H_2O$. One microgram (20 μl) of oligonucleotides #1138, 1139, 1140 and 1141 were phosphorylated in a volume of 100 μl using $T_4$ polynucleotide Kinase (11 units, Boehringer Mannheim) using 1 mM ATP and the buffer conditions recommended by the manufacturer for 12 hours and 40 minutes. The four Kinase reactions were boiled for one minute to inactivate Kinase, then pooled. One microgram (20 μl) of oligonucleotides #1137 and 1142 were added and the reaction volume was adjusted to 500 μl with the buffer recommended for $T_4$ DNA ligase. $T_4$ DNA ligase ($2 \times 10^6$ units, New England Biolabs) was added and the mixture was incubated at 15° C. for 12 hours. Analysis of an aliquot of the ligation by gel electrophoresis demonstrated the presence of a DNA fragment of approximately 100 bp as expected. The fragment contained the trpt sequence followed by restriction sites for XbaI, NarI, NcoI and SalI, respectively. The 3' end of the fragment contained components of the trp promoter. This promoter is present in order to promote transcription of the trpED stabilization genes in pGX2257 (see FIG. 1). The stabilization genes stabilize the plasmid in host strain GX1731 by plasmid complementation of host cell mutation.

Plasmid pGX2257 DNA was prepared from *E. coli* strain GX3003 (pGX2257) that contains a DNA adenine methylase (dam) mutation. *E. coli* strain GX1731 (pGX2257) has been deposited at the U.S. Department of Agriculture, Northern Regional Research Laboratory, Peoria, Ill., with accession No. NRRL B-15771. Any *E. coli* host with a dam mutation (A. Bale, M. D'Alarcao and M. G. Marinus, *Mutation Research*, 59:157165 (1979)) that is a λ phage lysogen can be utilized in place of GX3003 for this method. The pGX2257 DNA (15 μg) prepared in a dam host was digested with 8 units of HpaI endonuclease in 100 μl of the buffer recommended by the manufacturer at 37° C. for two hours. The DNA solution was then extracted with a 1:1 mixture of water saturated phenol and cloroform (adjusted to pH 8.0 with tris-[hydroxymethyl]-aminomethane base). The aqueous phase was adjusted to a 0.2 M sodium acetate pH 5.5 and 2.5 volume of 95% ethanol was added to precipitate the DNA. The ethanol solution was frozen using dry ice then centrifuged at 15,000 X G to precipitate the DNA. The DNA was dissolved in 30 μl H$_2$O to give a DNA concentration of 0.5 μg/μl.

Referring to FIG. 1, the ligated synthetic DNA described above was ligated to HpaI-cut pGX2257 DNA by addition of 5 μl(2.5 μg) of HpaI-cut pGX2257 to 60 μl (~0.72 μg) of the oligonucleotide ligation in a total reaction volume of 75 μl with 8×10$^5$ units of T$_4$ DNA ligase at 15° C. with 0.5 mM ATP for 12 hours. The ligation was phenol-chloroform extracted and ethanol precipitated as described above, then dissolved in 50 μl H$_2$O. The ligated DNA was then digested with 12 units of BclI endonuclease in 70 μl of buffer recommended by the manufacturer at 37° C. for 2 hours. The BclI digestion reaction was phenol-chloroform extracted and the DNA was precipitated as described above. The DNA pellet was dissolved in 80 μl of H$_2$O. The final ligation at low DNA concentration to circularize the DNA included 15 μl of the BclI-cut DNA in a 150 μl ligation reaction with 8×10$^5$ units of T$_4$ DNA ligase, 1 mM ATP in the recommended buffer at 15° C. for 12 hours. Aliquots of the final ligation reaction were used to transform *E. coli* GX1731 (F−, [λcI857-ΔBAMΔHI]Δ[chlA-pgl]nadA::Tn10 ΔtrpED102 tna2) using the standard calcium shock procedure. Plasmids in transformant colonies were screened using agarose gel electrophoresis looking for plasmids with decreased size relative to pGX2257 and the presence of XbaI, NarI, NcoI and SalI endonuclease sites that are located in the synthetic DNA. Cells containing plasmids with the correct endonuclease digestion pattern were tested for the ability to grow independent of tryptophan to demonstrate plasmid complementation of the host trp deletion. One plasmid with the proper characteristics was labeled pGX2287. Strain GX1731, transformed with pGX2287, was deposited at the U.S. Department of Agriculture, Northern Regional Research Laboratory, Peoria, Illinois, with accession No. NRRL B-15788.

EXAMPLE 2

Expression of trpB/Δ-2 Prochymosin

A series of fermentation runs was conducted, using host strain GX1731, transformed with either pGX2287 or its parental plasmid pGX2257. In each instance, a liquid nitrogen stored ampule of the transformant strain was thawed and 0.4 ml of the contents were inoculated into each of two 250 ml baffled flasks containing 50 ml of LB broth supplemented with 100 μg/ml ampicillin. The two flasks were incubated at 30° C. and 250 rpm in an incubator shaker for 6.5 to 9 hours.

Fermentation was carried out using 8 liters of the following initial medium:

| | |
|---|---|
| (NH$_4$)$_2$SO$_4$ | 30 g |
| KH$_2$PO$_4$ | 15 g |
| K$_2$HPO$_4$ | 5 g |
| Biotin (0.5 mg/ml in 95% Ethanol) | 12 ml |
| Tap water to 8 liters, autoclave | |

| | |
|---|---|
| CaCl$_2$.2H$_2$O | 10 ml of 10% (w/v) sterile solution |
| glucose | 360 ml of 50% (w/v) sterile solution |
| niacon | 18 ml of 0.5% (w/v) sterile solution |
| Trace solution 1 | 90 ml |
| Trace solution 2 | 18 ml |
| Trace solution 3 | 1.8 ml |

The following fermentation conditions were maintained:

| | |
|---|---|
| pH 7.0 (controlled by NH$_4$OH, 5N and H$_3$PO$_4$, 1N) | |
| Sparge rate | 1 vvm |
| Temperature | 32° C. |
| Agitation rate | 800 rpm |

The initial medium was inoculated with the contents of the baffled flask to a final volume of 9.0 liters.

In order to increase cell density prior to induction of expression, a system of broth supplementation with nutrients was undertaken. The feed solution was prepared as follows:

1000 g glucose with deionized water for final volume of 1700 mls was autoclaved. After autoclaving, there was added:

| | |
|---|---|
| Trace solution 1 | 500 ml |
| Trace solution 2 | 100 ml |
| Trace solution 3 | 10 ml |
| CaCl$_2$.2H$_2$O | 50 ml |
| Trace Solution #1 | |
| H$_2$O | 900 ml |
| conc HCl | 13.3 ml |
| FeCl$_3$.6H$_2$O | 5.4 g |
| ZnSO$_4$.7H$_2$O | 1.44 g |
| MnCl$_2$.4H$_2$O | 1.0 g |
| CuSO$_4$.5H$_2$O | 0.25 g |
| CoCl$_2$.6H$_2$O | 0.24 g |
| H$_3$BO$_3$ | 0.062 g |
| Brought to 1000 ml and sterile filtered | |
| Trace Solution #2 | |
| H$_2$O | 900 ml |
| HCl | 44.8 ml |
| MgSO$_4$.7H$_2$O | 61.6 g |
| Brought to 1000 ml and sterile filtered | |

| -continued | |
|---|---|
| Trace Solution #3 | |
| H₂O | 1000 ml |
| Na₂MoO₄.2H₂O | 24.1 g |
| Sterile filtered | |

The feed solution was initially added to the broth in a volume of 180 ml and thereafter as needed to maintain the glucose level at 10 g/liter. Feed supplementation was continued until the A₆₀₀ reached 20, at which time the cells were induced to express trpB/Δ-2 prochymosin. Induction was effected by raising the temperature to 42° C. to deactivate the temperature sensitive cI857 repressor protein. After one hour, the temperature was reduced to 39° C. for the remainder of the run (about six hours).

One-ml samples of cells from fermentors were placed in 1.5 ml Eppendorf tubes and centrifuged for 5 minutes. Cell pellets were resuspended in 1 ml of water, recentrifuged, and stored as pellets at −20° C.

Cell pellets were suspended in water at an A₆₀₀ of 10 in 15 ml Corex tubes. Two ml of cells at A₆₀₀ = 10 were lysed by sonication for 6 pulses of 30 seconds each. The suspension was kept on ice during sonication. The A₆₀₀ of uninduced cells was about 0.5 after sonication.

The cell sonicate was centrifuged at 8000 rpm for 15 minutes (SS34 rotor). The supernatant was discarded, and the pellet suspended in 90 μl of 10 mM EDTA by vortexing. 10 μl of 1 N NaOH was added, and the suspension was vortexed until it dissolved. There was added 0.8 ml of water followed by 0.1 ml of 0.1 M glycine, pH 7.5, and the solution was incubated overnight at room temperature. The pH at this point was 10.0. The pH was then adjusted to 2.0 by addition of about 20 μl of 1 N HCl. Incubation was continued for two hours at room temperature. Under these conditions, trpB/Δ-2 prochymosin underwent autocatalytic cleavage to produce mature, active chymosin.

Chymosin activity was evaluated by observing the formation of a parakappa casein precipitate following the catalytic cleavage of kappa casein to give parakappa casein and a small soluble glycoprotein. Chymosin activity was calculated from the time required for the absorbance at 600 nm (light scattering) of kappa casein substrate to reach 1.0. Activity is expressed relative to commercial single-strength rennet, which is used as a standard and defined to have an activity of 1.0 U/ml.

The results from each of four fermentation runs using a strain transformed with plasmid pGX2287 and four fermentation runs using a strain transformed with parental plasmid pGX2257, which lacks the trpt sequence, are given in the table below. It can be seen from the table that the strain transformed with plasmid pGX2287, which contains the trpt sequence immediately downstream from the translation termination signal of the Δ-2 prochymosin gene, produced several-fold higher titers of chymosin activity than the parental strain, pGX2257.

| Plasmid | Run | Chymosin Activity (Units/Liter) |
|---|---|---|
| pGX2257 | 1 | 35 |
|  | 2 | 22 |
|  | 3 | 18 |
|  | 4 | 23 |
| pGX2287 | 5 | 83 |
|  | 6 | 75 |
|  | 7 | 88 |
|  | 8 | 113 |

What is claimed is:

1. A method for expressing a gene encoding a desired protein in an *E. coli* host at elevated levels of expression, which comprises:
   (a) inserting a structural gene encoding a desired protein and the trpt sequence of the *E. coli* tryptophan operon into a vector replicable in an *E. coli* host, such that said sequence is adjacent to and downstream from the translation termination codon of said structural gene;
   (b) transforming said *E. coli* host with said vector; and
   (c) expressing said structural gene in the thus transformed *E. coli* host.

2. The method of claim 1, wherein said desired protein is a heterologous protein.

3. The method of claim 1, wherein said desired protein is a homologous protein other than *E. coli* tryptophan synthase A protein.

4. The method of claim 2, wherein said heterologous protein is prochymosin.

5. The method of claim 1, wherein said trpt sequence comprises the trpt sequence following the stop codon of the trpA gene.

6. The method of claim 5, wherein said trpt sequence is

ATCCCACAGCCGCCAGTTCCGCTGGCG-GCATTTT.

7. The method of claim 1, wherein said vector is the vector pGX2287.

8. The method of claim 1, wherein said *E. coli* host is *E. coli* strain GX1731.

9. The method of claim 1, wherein all or a portion of the transcribed but untranslated region normally present at the 3′ end of said structural gene is removed.

10. A replicable expression vector for expressing a desired protein in an *E. coli* host at elevated levels of expression, which comprises the trpt sequence of the *E. coli* tryptophan operon.

11. The vector of claim 10, wherein said trpt sequence comprises a 34 nucleotide sequence which follows the stop codon of said trpA gene.

12. The vector of claim 11, wherein said 34 nucleotide sequence comprises the following sequence:

ATCCCACAGCCGCCAGTTCCGCTGGCG-GCATTTT.

13. The vector of claim 10, further comprising a structural gene encoding a desired protein, wherein said first trpt sequence is adjacent to and downstream from the translation termination codon of said structural gene.

14. The vector of claim 13, wherein said desired protein is a heterologous protein.

15. The vector of claim 13, wherein said desired protein is a homologous protein other than *E. coli* tryptophan synthase A protein.

16. The vector of claim 14, wherein said heterologous protein is prochymosin.

17. The vector of claim 13, wherein said structural gene is devoid of all or a portion of the transcribed but untranslated region normally present at the 3′ end of said gene.

18. The vector of claim 10, wherein said vector is a plasmid.

19. The vector of claim 18, wherein said plasmid is pGX2287.

20. An *E. coli* host transformed with the vector of claim 10, 11, 12, 13, 14, 15, 16, 17, 18, or 19.

21. The *E. coli* host of claim 20, wherein said host is *E. coli* strain GX1731.

22. *E. coli* strain GX1731, transformed with vector pGX2287.

23. The plasmid pGX2287.

* * * * *